United States Patent [19]

Motoki et al.

[11] Patent Number: 5,206,379
[45] Date of Patent: Apr. 27, 1993

[54] α-ACYLMETHOXYCARBONYLBENZO-TRIAZOLES

[75] Inventors: Masuji Motoki; Seiji Ichijima; Keiji Mihayashi, all of Kanagawa, Japan

[73] Assignee: Fuji Photo Film Co., Ltd., Kanagawa, Japan

[21] Appl. No.: 751,839

[22] Filed: Aug. 29, 1991

[30] Foreign Application Priority Data

Nov. 7, 1990 [JP] Japan .................. 2-302079

[51] Int. Cl.$^5$ .................. C07D 401/10; C07D 249/18
[52] U.S. Cl. ................................ 548/261; 548/199
[58] Field of Search ............... 548/261; 546/199

[56] References Cited

U.S. PATENT DOCUMENTS 4,477,563 10/1984 Ichijima et al. .................. 430/544
4,812,389 3/1989 Sakanoue et al. .................. 430/382
5,004,677 4/1991 Ueda .................................. 430/382

FOREIGN PATENT DOCUMENTS 0167168 1/1986 European Pat. Off. ............ 430/382

Primary Examiner—Mary C. Lee
Assistant Examiner—Joseph K. McKane
Attorney, Agent, or Firm—Sughrue, Mion, Zinn, Macpeak & Seas

[57] ABSTRACT

Acylmethoxycarbonylbenzotrizoles with an ester substituent are disclosed which are represented by formula (I):

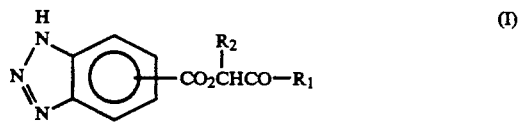

wherein $R_1$ is an aliphatic oxy group having 1-10 carbons or an aliphatic amino group having 2-10 carbons; $R_2$ is hydrogen or an aliphatic group having 1-5 carbons; and the group

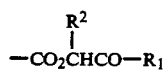

is bonded to a 5- or 6-position of the benzotriazole and which are useful in silver halide photographic sensitive materials, synthesis intermediates therefor, synthesis intermediates for medicines, rust inhibitors for metals and the like.

6 Claims, No Drawings

α-ACYLMETHOXYCARBONYLBENZO-TRIAZOLES

FIELD OF THE INVENTION

The present invention relates to α-acylmethoxycarbonyl-benzotriazoles which are useful in silver halide photographic sensitive materials, synthesis intermediates therefor, synthesis intermediates for medicines, rust inhibitors for metals and the like.

BACKGROUND OF THE INVENTION

Benzotriazoles having an ester linkage as a substituent have been known and used in silver halide photographic sensitive materials, synthesis intermediates therefor, synthesis intermediates for medicines, rust inhibitors for metals, and the like. Examples of rust inhibitors are described in U.S. Pat. Nos. 4,187,186 and 4,522,785; medicine synthesis intermediates are described in JP-A-52-100473 (the term "JP-A" as used herein means "Unexamined Published Japanese Patent Application"); and examples of synthesis intermediates of photographic compounds are described in U.S. Pat. No. 4,477,563.

Although phenoxycarbonylbenzotriazole, described in the above-cited U.S. Pat. No. 4,477,563, is used currently as a synthesis intermediate for a coupler in color photography, there are disadvantages such that photographic performance is not sufficient and phenol used as the synthesis starting material irritates human skin thereby making troublesome the handling of the substance in production.

SUMMARY OF THE INVENTION

The present invention intends to provide a benzotriazole having an ester substituent which is superior in photographic performances, limited less in production and suitable for mass-production.

The present invention provides an α-acylmethoxycarbonylbenzotriazole represented by formula (I):

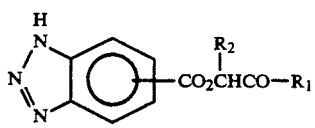
(I)

wherein $R_1$ is an aliphatic oxy group having 1–10 carbons or an aliphatic amino group having 2–10 carbons; $R_2$ is hydrogen or an aliphatic group having 1–5 carbons; and the group $$-CO_2CHCO-R_1$$
$$\overset{|}{R_2}$$

is bonded to a 5- or 6-position of the benzotriazole.

DETAILED DESCRIPTION OF THE INVENTION

In the present invention, the aliphatic group includes methyl, ethyl, propyl, butyl, isobutyl, 1-methyl-propyl, 1,2-dimethylpropyl, 1-methylbutyl, 2-methylpropyl, 2-methylbutyl, pentyl, isopentyl, 1-ethylpropyl, cyclopentyl, 2-ethylbutyl, 3-butenyl, hexyl, octyl, cyclohexyl, decyl and the like.

The aliphatic amino group includes amino groups having the above-mentioned aliphatic group or cyclic amino groups. The cyclic amino group is exemplified by pyrrolidino and piperidino.

Of the compounds represented by formula (I), $R_1$ is preferably an aliphatic oxy group of 4–8 carbons or an aliphatic amino group having 5–8 carbons. More preferably $R_1$ is an aliphatic oxy group of 5–8 carbons. $R_2$ is preferably hydrogen.

The compounds of the present invention are exemplified specifically below without limiting the invention.

Exemplified compounds

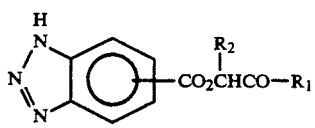

| No. | $R_1$ | $R_2$ | Melting point (°C.) |
|---|---|---|---|
| (1) | $-OC_4H_9$ | H | 80–82 |
| (2) | $-OCHC_2H_5$<br>$\quad\mid$<br>$\quad CH_3$ | H | 82–83 |
| (3) | $-OCH_2CHCH_3$<br>$\qquad\mid$<br>$\qquad CH_3$ | H | 96–97 |
| (4) | $-OC_4H_9$ | $CH_3$ | 48–49 |
| (5) | $-OC_5H_{11}$ | H | 71–72 |
| (6) | $-OCH_2CH_2CHCH_3$<br>$\qquad\qquad\mid$<br>$\qquad\qquad CH_3$ | H | 77–78 |
| (7) | $-OCH(CH_2)_2CH_3$<br>$\quad\mid$<br>$\quad CH_3$ | H | 81–82 |
| (8) | $-OCHC_2H_5$<br>$\quad\mid$<br>$\quad C_2H_5$ | H | 95–96 |
| (9) | $-OCH-CHCH_3$<br>$\quad\mid\quad\;\mid$<br>$\;\;CH_3\;CH_3$ | H | 84–85 |
| (10) | $-OCH_2CHC_2H_5$<br>$\qquad\mid$<br>$\qquad CH_3$ | H | 55–57 |
| (11) | $-OCH_2C(CH_3)_3$ | H | 65–66 |
| (12) | $-OCH_2CHC_2H_5$<br>$\qquad\mid$<br>$\qquad OCH_3$ | H | Oil |
| (13) | 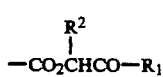 | H | 79–81 |
| (14) | $-OC_8H_{17}$ | H | 62–63 |
| (15) | $-NHC_5H_{11}$ | H | 133–134 |
| (16) | $-NHC_6H_{13}$ | H | 131–132 |
| (17) | $-N\begin{matrix}\diagup C_2H_5\\\diagdown C_2H_5\end{matrix}$ | H | 64–65 |
| (18) | $-N\begin{matrix}\diagup C_2H_5\\\diagdown C_3H_7\end{matrix}$ | H | 124–125 |

-continued
Exemplified compounds

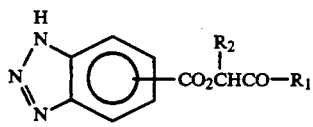

| No. | R₁ | R₂ | Melting point (°C.) |
|---|---|---|---|
| (19) | −N(C₃H₇)(C₃H₇) | H | 150–151 |
| (20) | −N(piperidine) | H | 150–151 |
| (21) | −OC₄H₉ | −C₃H₇ | Oil |

The compound of the present invention may be synthesized through the route shown below.

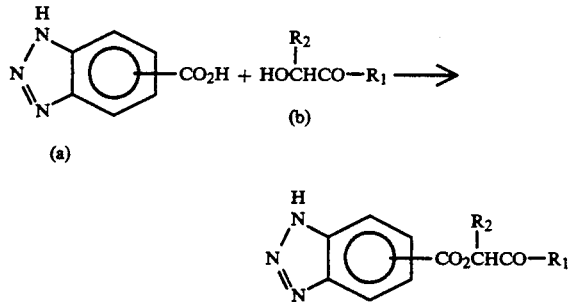

In the formula, $R_1$ and $R_2$ are respectively the same as in formula (I). The compound (a) can be synthesized according to the method described in U.S. Pat. No. 4,477,563.

The reaction of the compound (a) with the compound (b) is conducted generally in the presence of a dehydrating-condensing agent. The preferable dehydrating-condensing agent includes a carbodiimide such as N,N′-dicyclohexylcarbodiimide and N,N′-diisopropylcarbodiimide; a carbonyldiimidazole. Otherwise, the dehydration reaction can be conducted in the presence of an acid catalyst such as concentrated sulfuric acid, hydrochloric acid and p-toluenesulfonic acid. In another method of synthesis, the compound (a) is converted to an acid chloride which is then reacted with the compound (b) in the presence or absence of a base (e.g., triethylamine, pyridine). The use of a derivative (e.g., mixed acid anhydride) equivalent to the acid chloride gives the same result.

The compound of the present invention also can be synthesized by use of a compound which is derived by replacing the hydroxyl group with a halogen in the compound (b).

The solvent for the reaction may be any of generally used aprotic solvents. The aprotic solvents include esters such as ethyl acetate and butyl acetate; nitriles such as acetonitrile and propionitrile; amides such as N,N-dimethylformamide, N,N-dimethylacetamide and N-methylpyrrolidone; halogenated hydrocarbons such as chloroform and methylene chloride; and aromatics such as benzene, toluene and chlorobenzene.

The methods of synthesis of typical compounds of the present invention are described specifically below.

EXAMPLE 1: Syntesis of Exemplified Compound (6)

Exemplified compound (6) was synthesized through the synthesis route below:

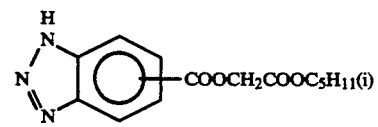

Exemplified compound (6)

Step (1): Synthesis of Intermediate compound a 50 grams (0.658 moles) of glycolic acid and 87 grams (0.986 ;moles) of isopentanol were dissolved in 300 ml of n-hexane. Thereto, 3 ml of concentrated sulfuric acid was added gradually dropwise at room temperature with stirring. The mixture was allowed to undergo reaction at reflux temperature for 2 hours by eliminating the formed water by use of a Dean-Stark trap. Having been cooled with water, the reaction mixture was added to 200 ml of water and thereto 300 ml of ethyl acetate was added. The mixture was neutralized by addition of sodium bicarbonate. The ethyl acetate and the n-hexane were evaporated off under reduced pressure. The evaporation residue was distilled under reduced pressure to obtain 77.4 g (77.4%) of the oily intermediate compound (a) having a boiling point of 85°–95° C./18mmHg. The structure was confirmed by mass spectrometry.

Step (2): Synthesis of Exemplified Compound (6)

21.2 grams (0.145 mole) of intermediate compound a, 23 grams (0.141 mole) of 5-carboxylbenzotriazole and 0.7 gram (0.0057 mole) of 4-N,N-dimethylaminopyridine were dissolved in a mixed solvent of 40 ml N,N-dimethylformamide and 60 ml acetonitrile. Thereto, a solution of 29.1 g (0.141 mole) of dicyclohexylcarbodiimide in 20 ml acetonitrile was added dropwise at room temperature with stirring over 10 minutes. The mixture was allowed to react at a temperature of 50°–60° C. for 2 hours and then cooled with water. The precipitated dicyclohexylurea was removed by filtration. The filtrate was poured into a mixture of 300 ml water and 150 ml ethyl acetate. The mixture was washed with water. The ethyl acetate was evaporated off under reduced pressure. The residue was dissolved by heating in a mixed solvent of 50 ml ethyl acetate and 50 ml n-hexane. The insoluble matter was eliminated. The solvent was evaporated under reduced pressure. To the concentrated matter, a mixed solvent of 15 ml ethyl acetate and 150 ml n-hexane was added and heated to dissolve it. After the solution was cooled, the deposited crystalline matter was collected by filtration to obtain 32.2 g (yield: 78.4%) of the intended exempliiied compound (6). The structure was confirmed by mass spectrometry. The melting point of the resulting compound was 77°–78° C.

EXAMPLE 2: Synthesis of Exemplified Compound (16)

Exemplified compound (16) was synthesized through the synthesis route shown below.

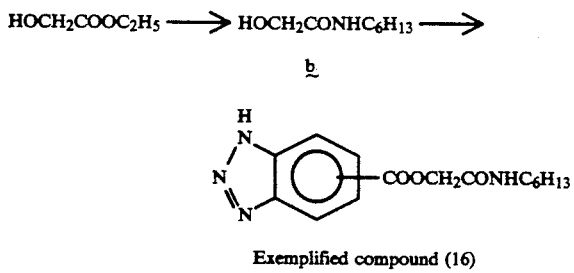

Exemplified compound (16)

Step (1): Synthesis of intermediate compound b 22 grams (0.211 mole) of ethyl glycolate was stirred under water cooling. Thereto, 23.5 g (0.232 mole) of n-hexylamine was added dropwise in 5 minutes. After stirring for 1 hour at room temperature, the mixture was stirred further at 50°-60° C. for 2.5 hours. The ethanol formed by the reaction and excess n-hexylamine was evaporated under reduced pressure to obtain 33.5 g (yield: 99.7%) of oily intermediate compound b.

Step (2): Synthesis of Exemplified Compound (16)

20.1 grams (0.126 mole) of the intermediate compound b obtained in Step (1), 20 grams (0.123 mole) of 5-carboxyl-benzotriazole and 0.6 gram (0.005 mole) of 4-N,N-dimethyl-aminopyridine were dissolved in a mixed solvent of 40 ml of N,N-dimethylformamide and 60 ml acetonitrile. Thereto, a solution of 25.3 g (0.123 mole) of dicyclohexylcarbodiimide in 20 ml of acetonitrile was added dropwise with stirring at room temperature over 10 minutes. The mixture was allowed to undergo reaction at a temperature of 50°-60° C. for 2 hours and cooled with water. The precipitated cyclohexylurea was removed by filtration. The filtrate was poured into a mixture of 200 ml water and 120 ml ethyl acetate. The ethyl acetate layer was washed with water and an insoluble matter deposited in the ethyl acetate layer was removed. The ethyl acetate was distilled off under reduced pressure. The residue was recrystallized from a mixed solvent of 150 ml ethyl acetate and 100 ml h-hexane to obtain 29.3 g (yield: 78.4%) of Exemplified compound (16). The structure was confirmed by mass spectrometry. The melting point was 131°-132° C.

The benzotriazoles of the present invention are useful as a leaving group of DIR couplers in silver halide photosensitive materials for color photography.

APPLICATION EXAMPLE 1

A synthesis example of a DIR coupler employing the benzotriazoles of the present invention is shown below.

A DIR coupler was synthesized through the route below:

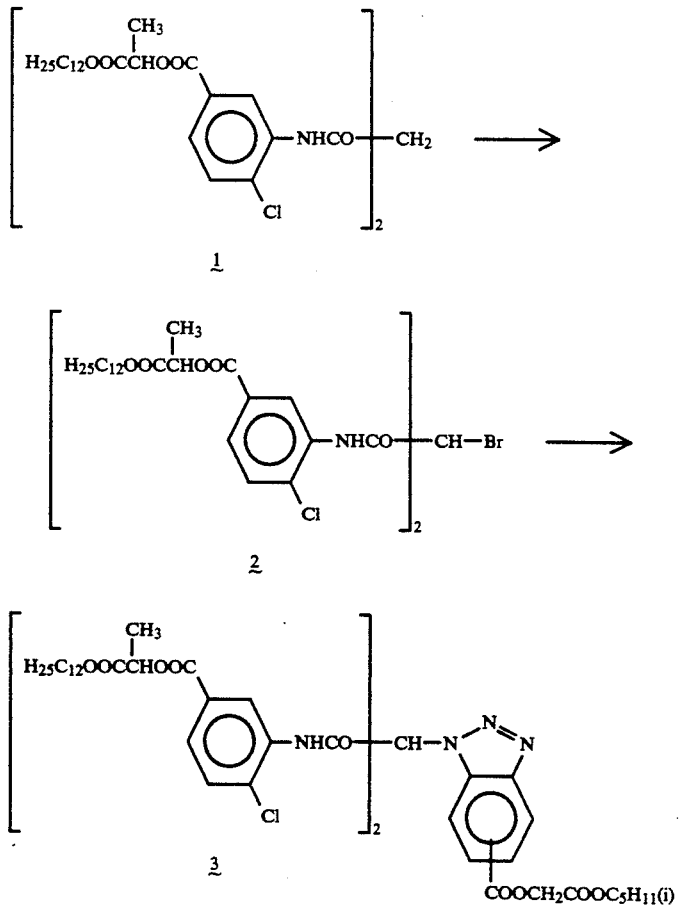

Step (1): Synthesis of Intermediate Compound 2

To 35 g (0.039 mole) of Compound 1 dissolved in 60 ml of methylene chloride, 6.5 g (0.0406 mole) of bromine was added dropwise with stirring with water cooling over 10 minutes. The mixture was stirred at a temperature of 23° C. or lower for 10 minutes. The methylene chloride solution was washed with water three times, thereby obtaining a solution of Compound 2 in methylene chloride.

Step (2): Synthesis of Final Compound 3

A solution of Compound 2 (0.039 mole) in methylene chloride prepared in Step (2) was added dropwise to a solution of 25.7 g (0.088 mole) of Exemplified compound (6) and 12.3 ml (0.088 mole) of triethylamine in 70 ml of N,N-dimethylformamide with stirring and water cooling over 30 minutes. The mixture was stirred at a temperature not higher than 25° C. for one hour. Thereto 100 ml of ethyl acetate was added. The ethyl acetate-methylene chloride layer was washed twice with a solution of 10 g (0.094 mole) of anhydrous sodium carbonate in 200 ml of water. The washed organic layer was acidified by addition of aqueous hydrochloric acid solution and washed twice with water. The organic layer was dried over sodium sulfate and the organic solvent was distilled off at a reduced pressure. The residual oily matter was dissolved in 200 ml of isopropyl alcohol by heating. The solution was left standing at room temperature for 3 hours. The deposited crystalline matter was collected by filtration to obtain 30.9 (yield: 67.0%) of the final compound 3. The structure was confirmed by mass spectrometry. The melting point was 85°–87° C.

APPLICATION EXAMPLE 2

A silver halide photosensitive material for color photography (Sample 1) was prepared which is identical with the sensitive material 1 in Example 1 of JP-A-2-93641.

To the sensitive material, a white imagewise exposure was applied at a maximum exposure of 5 lux sec. The material was treated according to the method described in Table 1. In the treatment, the color development solutions (A) - (H) were prepared by addition of 10 ml of a 0.02 ml/l methanol solution of the compound shown in Table 2 per 1 liter of the developing solution. The treatment was conducted in two ways: development being started immediately after the addition (10 seconds after the addition) and development being started 30 minutes after the addition.

After the treatment, the sensitivity and developed color density of the yellow image was measured. The results are shown in Table 2.

TABLE 1

Treating method

| Steps | Treating time | Treating temperature |
|---|---|---|
| Color development (A)–(H) | 3 min 15 sec | 38° C. |
| Bleaching | 6 min 30 sec | 38° C. |
| Water washing | 2 min 10 sec | 24° C. |
| Fixing | 4 min 20 sec | 38° C. |
| Water washing (1) | 1 min 05 sec | 24° C. |
| Water washing (2) | 1 min 00 sec | 24° C. |
| Stabilizing | 1 min 05 sec | 38° C. |
| Drying | 4 min 20 sec | 55° C. |

The composition of the treating solutions is shown below.

(Unit: g)

| (Color developing solution) | |
|---|---|
| Diethylenetriaminepentaacetic acid | 1.0 |
| 1-Hydroxyethylidene-1,1-diphosphonic acid | 3.0 |
| Sodium sulfite | 4.0 |
| Potassium carbonate | 30.0 |
| Potassium bromide | 1.4 |
| Potassium iodide | 1.5 mg |
| Hydroxylamine sulfate | 2.4 |
| 4-[N-ethyl-N-β-hydroxyethylamino]-2-methylaniline sulfate | 4.5 |
| Water to make | 1.0 liter |
| pH | 10.05 |
| (Bleaching solution) | |
| Ferric sodium ethylenediamine-tetraacetatetrihydrate | 100.0 |
| Disodium ethylenediaminetetraacetate | 10.0 |
| Ammonium bromide | 140.0 |
| Ammonium nitrate | 30.0 |
| Aqueous ammonia (27%) | 6.5 ml |
| Water to make | 1.0 liter |
| pH | 6.0 |
| (Fixing solution) | |
| Disodium ethylenediaminetetraacetate | 0.5 |
| Sodium sulfite | 7.0 |
| Sodium bisulfite | 5.0 |
| Aqueous ammonium thiosulfate (70%) | 170.0 ml |
| Water to make | 1.0 liter |
| pH | 6.7 |
| (Stabilizing solution) | |
| Formalin (37%) | 2.0 ml |
| Polyoxyethylene-p-mononoylphenyl ether (Average polymerization degree: 10) | 0.3 |
| Disodium ethylenediaminetetraacetate | 0.05 |
| Water to make | 1.0 liter |
| pH | 5.0–8.0 |

TABLE 2

| | Added compound | | 10 seconds after addition | | 30 minutes after addition | | |
|---|---|---|---|---|---|---|---|
| | Kind | [mol/l] | Relative[1] sensitivity | Developed[2] color density | Relative[1] sensitivity | Developed[2] color density | Remarks |
| A | — | — | 0.00 | 2.82 | 0.00 | 2.82 | Control |
| B | R-1 | $5 \times 10^{-6}$ | −0.51 | 2.52 | −0.52 | 2.51 | Comparison |
| C | R-2 | $1 \times 10^{-4}$ | −0.43 | 2.45 | −0.42 | 2.46 | Comparison |
| D | R-3 | " | −0.32 | 2.57 | −0.12 | 2.70 | Comparison |
| E | (1) | " | −0.37 | 2.50 | 0.00 | 2.81 | Invention |
| F | (5) | " | −0.47 | 2.42 | −0.02 | 2.79 | Invention |
| G | (6) | " | −0.45 | 2.44 | −0.01 | 2.79 | Invention |

TABLE 2-continued

| Added compound | | 10 seconds after addition | | 30 minutes after addition | | |
| --- | --- | --- | --- | --- | --- | --- |
| Kind | [mol/l] | Relative[1] sensitivity | Developed[2] color density | Relative[1] sensitivity | Developed[2] color density | Remarks |
| H | (8) | " | −0.44 | 2.46 | −0.01 | 2.80 | Invention |

[1] A relative value of a reciprocal of exposure giving a density of (fog + 0.2)
[2] Density of yellow at the exposure of 1 lux · sec Structural formulas of Comparative compounds:

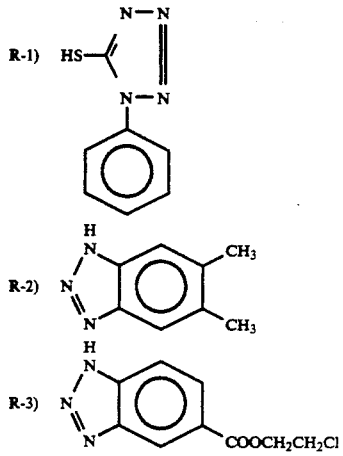

R-1), R-2), R-3)

Table 2 shows that the compound of the present invention gives satisfactory effect of development inhibition immediately after the addition but gives almost no effect 30 minutes after the addition. Therefore, it is obvious that the compound of the present invention is superior as a deactivation-type development inhibitor.

APPLICATION EXAMPLE 3

A sample identical to sample 201 of Example 2 disclosed in JP-A-2-90151 was prepared. The sample was tested in the same manner as the instant Application Example 2 by using it in place of the sample of Application Example 2. The results were similar to those in Application Example 2.

APPLICATION EXAMPLE 4

Each 300 mg of the comparative compounds and the compounds of the present invention used in Application Example 2 were taken in a Petri dish respectively and were left standing for 4 weeks under the conditions of 60° C. and a relative humidity of 30%. Thereafter, the samples were tested in the same manner as in Application Example 2. The test results were almost the same as in Application Example 2, which shows that the compounds of the present invention lose the development inhibition activity in a color developing solution at a suitable rate, but are stable in an isolated state.

APPLICATION EXAMPLE 5

Sample 2 was prepared by incorporating the Comparative compound (R-2) in an amount of 0.9 mg/m² into each of the 5th, 7th, 9th, 11th and 12th layers of Sample 1. In the same manner Samples 3-5 were prepared by using respectively (R-3), and Compounds (6) and (7) of the present invention.

The Samples 1-5 were slit in a width of 35 mm to prepare the films each of 135 size format of 36 exposures. The films were loaded on a camera α-7000 (made of Minolta Camera Co., Ltd.), and distant views were photographed at a setting of ISO400 using a 35-105mm zoom lens at 105 mm. The 101 films of the respective Samples 1-5 were treated continuously for development as shown below.

The sensitivities and the developed color densities were measured with the first and 101st films in the continuous treatment. The results are shown in Table 3.

| | Treating Method | | | |
| --- | --- | --- | --- | --- |
| Steps | Treating time | Treating temperature | Replenisher* | Tank volume |
| Color development | 3 min 15 sec | 37.8° C. | 25 ml | 10 l |
| Bleaching | 45 sec | 38° C. | 5 ml | 4 l |
| Bleach-fix (1) | 45 sec | 38° C. | — | 4 l |
| Bleach-fix (2) | 45 sec | 38° C. | 30 ml | 4 l |
| Water washing (1) | 20 sec | 38° C. | — | 2 l |
| Water washing (2) | 20 sec | 38° C. | 30 ml | 2 l |
| Stabilizing | 20 sec | 38° C. | 20 ml | 2 l |
| Drying | 1 min | 55° C. | | |

*The amount of replenishing for 1 m length, 35 mm width

The steps of bleach-fix and water washing are respectively of a counter-current type of from (2) to (1), and the overflow of the bleaching liquid was all introduced to the bleach-fix (2).

In the aforementioned treatment, the quantity of the bleach-fix solution carried over into the washing step was 2 ml for 1 m length and 35 mm width of the sensitive material.

| | Tank solution (g) | Replenisher (g) |
| --- | --- | --- |
| (Color developing solution) | | |
| Diethylenetriaminepentaacetic acid | 5.0 | 6.0 |
| Sodium sulfite | 4.0 | 5.0 |
| Potassium carbonate | 30.0 | 37.0 |
| Potassium bromide | 1.3 | 0.5 |
| Potassium iodide | 1.2 mg | — |
| Hydroxylamine sulfate | 2.0 | 3.6 |
| 4-[N-ethyl-N-β-hydroxyethylamino]-2-methylaniline sulfate | 4.7 | 6.2 |
| Water to make | 1.0 l | 1.0 l |
| pH | 10.00 | 10.15 |
| (Bleaching solution) | | |

|  | Tank solution (g) | Replenisher (g) |
| --- | --- | --- |
| Ferric ammonium 1,3-diaminopropane-tetraacetate monohydrate | 144.0 | 206.0 |
| 1,3-diaminopropanetetraacetic acid | 2.8 | 4.0 |
| Ammonium bromide | 84.0 | 120.0 |
| Ammonium nitrate | 17.5 | 25.0 |
| Aqueous ammonia (27%) | 10.0 | 1.8 |
| Acetic acid (98%) | 51.1 | 73.0 |
| Water to make | 1.0 l | 1.0 l |
| pH | 4.3 | 3.4 |
| (Bleach-fixing solution) | | |
| Ferric ammonium ethylenediamine-tetraacetate dihydrate | 50.0 | — |
| Disodium ethylenediaminetetraacetate | 5.0 | 25.0 |
| Ammonium sulfite | 12.0 | 20.0 |
| Aqueous ammonium thiosulfate (700 g/l) | 290.0 ml | 320.0 ml |
| Aqueous ammonia (27%) | 6.0 ml | 15.0 ml |
| Water to make | 1.0 l | 1.0 l |
| pH | 6.8 | 8.0 |

(Washing water) Common to tank solution and replenisher:

City water was passed through a mixed bed column packed with an H-type strongly acidic cation exchange resin (Amberlite IR-120B made by Rohm and Haas Co.) and an OH-type strongly basic anion exchange resin (Amberlite IRa-400 made by the same company) to reduce the calcium and magnesium content to 3 mg/l or lower, and thereto 20 mg/l of sodium dichloroisocyanurate cyanurate and 150 mg/l of sodium sulfate were added. The pH of the water was within the range of from 6.5 to 7.5.

|  | (Unit; g) |
| --- | --- |
| (Stabilizing solution) Common to tank solution and replenisher: | |
| Formalin (37%) | 1.2 ml |
| Surfactant [C$_{10}$H$_{21}$—O—(CH$_2$CH$_2$O)$_{10}$—H] | 0.4 |
| Ethylene glycol | 1.0 |
| Water to make | 1.0 l |
| pH | 5.0–7.0 |

TABLE 3

|  | First Film | | 101st Film | | |
| --- | --- | --- | --- | --- | --- |
| Compound | Relative[1] sensitivity | Developed[2] color density | Relative[1] sensitivity | Developed[2] color density | Remarks |
| 1 — | 0.00 | 2.90 | −0.02 | 2.83 | Control |
| 2 (R-2) | −0.10 | 2.73 | −0.24 | 2.57 | Comparison |
| 3 (R-3) | −0.11 | 2.72 | −0.18 | 2.64 | Comparison |
| 4 (6) | −0.11 | 2.72 | −0.12 | 2.71 | Invention |
| 5 (16) | −0.12 | 2.70 | 0.15 | 2.67 | Invention |

[1] and [2] The definition is the same as in Table 2.

From Table 3, it is obvious that the compound of the present invention have sufficient development-inhibiting ability and the performance of a treating solution after continuous treatment of the sensitive materials containing the compounds of the present invention deteriorates less during continuous treatment.

The compound of the present invention is useful particularly as a synthesis starting material of a DIR couplers for sensitive material in color photography. The benzotriazole of the present invention is useful as a development inhibitor which is released by reaction of a DIR coupler with an oxidized form of a developing agent. Photographic properties such as a development-inhibition degree can be varied readily to be within a desired range by changing the groups of R$_1$ and R$_2$. The preferable degree of development inhibition depends on the kind of the sensitive material, the development treatment conditions and so forth. Accordingly, a suitable compound for the object can be selected readily from compounds, which is one advantage of the present invention.

A further advantage of the use of the compound of the present invention as a development-inhibiting agent is that the ester linkage is hydrolyzed in a development solution. The principle is described in detail in U.S. Pat. No. 4,477,563. When a sensitive material containing a DIR coupler is treated for development, a portion of the released development inhibitor goes into the developing solution and accumulates therein. After treatment of a large amount of sensitive material, the accumulated development-inhibiting agent becomes significant in amount, becoming great enough to inhibit development. Consequently, the treating liquid will not give constant sensitivity and gradation disadvantageously. However, with the DIR coupler releasing the development inhibitor of the present invention, the development inhibitor having entered the developing solution is decomposed so as not to inhibit the development. The rate of the decomposition is readily adjusted by selection of the groups of R$_1$ and R$_2$.

By use of the compound of the present invention, each of the intensity and the deactivation rate of development inhibition in a developing solution can be adjusted readily by selection of R$_1$ and R$_2$. On the contrary, conventional phenyl ester type of compounds are limited in the freeness in the adjustment disadvantageously.

A further advantage is that the compound of the present invention removes the disadvantage of skin irritation caused by phenol which is a starting material of the conventional phenyl ester type, whereby limitation in production is reduced and mass production is facilitated.

While certain embodiments have been disclosed in detail herein, it will be evident to the artisan that various changes and altenations can be made to the invention disclosed herein without departing from the spirit thereof and thus are to be considered equivalent thereto.

What is claimed is:

1. An α-acylmethoxycarbonylbenzotriazole represented by formula (I):

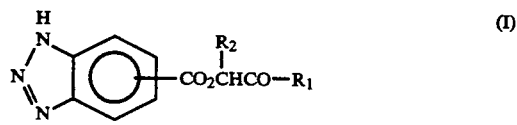

wherein R$_1$ is an aliphatic oxy group having 1–10 carbons or an aliphatic amino group having 2–10 carbons;

$R_2$ is hydrogen or an aliphatic group having 1-5 carbons; and the group

is bonded to a 5- or 6-position of the benzotriazole.

2. The α-acylmethoxycarbonylbenzotriazole of claim 1, wherein $R_1$ is an aliphatic oxy group of 4-8 carbons or an aliphatic amino group of 5-8 carbons.

3. The α-acylmethoxycarbonylbenzotriazole of claim 1, wherein $R_1$ is an aliphatic oxy group of 5-8 carbons.

4. The α-acylmethoxycarbonylbenzotriazole of claim 1, wherein $R_2$ is hydrogen.

5. The α-acylmethoxycarbonylbenzotriazole of claim 2, wherein $R_2$ is hydrogen.

6. The α-acylmethoxycarbonylbenzotriazole of claim 3, wherein $R_2$ is hydrogen.

* * * * *